(12) United States Patent
Mueller et al.

(10) Patent No.: US 7,005,090 B2
(45) Date of Patent: Feb. 28, 2006

(54) METHOD FOR MANUFACTURING A FLOW CELL

(75) Inventors: Jochen Mueller, Karlsruhe (DE); Beno Mueller, Ettlingen (DE)

(73) Assignee: Agilent Technologies, Inc., Palo Alto, CA (US)

( * ) Notice: Subject to any disclaimer, the term of this patent is extended or adjusted under 35 U.S.C. 154(b) by 418 days.

(21) Appl. No.: 10/217,070

(22) Filed: Aug. 12, 2002

(65) Prior Publication Data

US 2003/0076491 A1    Apr. 24, 2003

(30) Foreign Application Priority Data

Oct. 24, 2001   (EP)   ................... 01125224

(51) Int. Cl.
*B29D 11/00*   (2006.01)

(52) U.S. Cl. ............. 264/1.25; 264/516; 264/269; 356/246

(58) Field of Classification Search ........... 264/1.1, 264/1.25, 1.36, 269, 516, 1.7; 425/808; 356/246; 422/82.05, 102, 104
See application file for complete search history.

(56) References Cited

U.S. PATENT DOCUMENTS

| | | | |
|---|---|---|---|
| 4,329,879 A | 5/1982 | Appel et al. | ............. 73/861.12 |
| 4,950,446 A * | 8/1990 | Kinumoto et al. | ........... 264/516 |
| 5,444,807 A | 8/1995 | Liu | ............................ 385/125 |
| 5,608,517 A | 3/1997 | Munk | ......................... 356/246 |
| 6,188,813 B1 | 2/2001 | Dourdeville et al. | .......... 385/12 |
| 6,678,051 B1 * | 1/2004 | Gerner et al. | ............... 356/436 |

FOREIGN PATENT DOCUMENTS

| | | |
|---|---|---|
| DE | 714105 | 3/1952 |
| EP | 0 523 680 | 1/1993 |
| EP | 0 581 017 | 2/1994 |
| JP | 03038324 | 2/1991 |
| WO | WO 97/12209 | 4/1997 |

OTHER PUBLICATIONS

Mason, W., Examiner. European Search Report EP 01 12 5224 dated Mar. 18, 2002.

* cited by examiner

*Primary Examiner*—Mathieu D. Vargot

(57)   ABSTRACT

A method of manufacturing a flow cell with a cell housing having a bore for the passage of sample, and with an inner layer of a totally reflecting polymer material for guiding radiation through the bore for the analysis of the sample, comprises the steps of: a) providing a tube of the polymer material in the bore of the cell housing, and b) applying a force on the walls of the tube from the interior of the tube for pressing the walls of the tube against the cell housing. The force may be applied by any suitable means, for example by drawing a mandrel through the interior of the tube, or by using pressurized gas or liquid. The resulting flow cell has a smooth inner surface with improved optical properties.

14 Claims, 3 Drawing Sheets

METHOD FOR MANUFACTURING A FLOW CELL

The invention relates to a method for manufacturing a flow cell with an inner layer of a totally reflecting polymer material for guiding radiation through a bore of the flow cell.

BACKGROUND OF THE INVENTION

Flow cells are typically used in optical detectors for measuring the optical characteristics of a sample liquid flowing through the flow cell. Such detectors with the corresponding flow cell are used, for example, in liquid chromatography, or in capillary electrochromatography, or capillary electrophoresis, for determining the identity and concentration of sample substances. Ultraviolet (UV) and visible (Vis) light detectors wherein the absorbance of a sample in the flow cell is measured are frequently used for the mentioned separation techniques. Known flow cells are typically made of steel or quartz and have a cylindrical bore through which the liquid flows and through which light for analyzing the sample is directed.

It is important that a detector has: a) a high measuring sensitivity in order to be able to detect small sample amounts, and b) a small flow cell volume in order to ensure satisfactory peak resolution. Unfortunately, these are conflicting requirements since in the mentioned flow cells an increase of the sensitivity at constant cell volume leads to a reduction of the light conductivity value which in turn increases the noise and thus limits the detection limit. A solution to this problem consists in the use of flow cells employing total internal reflection of the light transmitted through the flow cell. This is achieved by coating the internal walls of the flow cell with a polymer having an index of refraction below that of water. A suitable polymer for this purpose is an amorphous fluoropolymer such as Teflon® AF (trademark of Dupont ). Due to the loss-free reflection in these cells, the light conductivity value is not reduced, so that the pathlength of the cell can be increased without loss in light throughput. Flow cells using the principle of total internal reflection are known from U.S. Pat. No. 5,184,192, U.S. Pat. No. 5,444,807, U.S. Pat. No. 5,608,517, and U.S. Pat. No. 6,188,813.

The mentioned patents also describe different methods for manufacturing the flow cells. According to U.S. Pat. No. 5,608,517, a mandrel is used which is coated with Teflon AF by multiple dipping into a corresponding solution and subsequent curing. The coated mandrel is then inserted into a housing comprising a heat shrinkable tubing. This tubing comprises an inner melting layer. The assembly is then heated to shrink the outer layer and to melt the inner layer. The melting inner layer fuses to the Teflon AF layer on the mandrel upon cooling. The mandrel is then removed from the flow passage leaving the Teflon AF layer fused and bonded to the inner layer. A shrinking step has disadvantages, because any inhomogeneities in the shrinking material lead to bending of the Teflon AF tube which causes a deterioration of the light throughput. In addition, the known process is complicated and costly because measures have to be taken to prevent damage of the Teflon AF layer when removing the mandrel and to ensure that the Teflon layer remains stable after removal of the mandrel.

According to U.S. Pat. No. 6,188,813, a molding step is employed. This, however, has the disadvantage that due to the direction of inflow and the mass of the molding material the soft Teflon AF tube may be deformed during the molding step, particularly with long cells. A consequence is that the optical properties, in particular the total reflection properties, are impaired. If there is a local unevenness in the Teflon AF material, the reflection angles will increase due to increased scattering so that the critical angle for total reflection is exceeded. The result is the loss of light and thus unwanted influences on the signal, for example an increase in the sensitivity to refractive index changes.

SUMMARY OF THE INVENTION

It is thus an object of the invention to provide a method for manufacturing a flow cell with a totally reflecting inner layer which avoids the mentioned problems of existing manufacturing methods.

Specifically, it is an object of the invention to provide a comparatively simple manufacturing method resulting in a flow cell having improved optical properties.

According to the invention, these objects are achieved by a manufacturing method as defined in claim 1. According to an important aspect of the invention, a tube of totally reflecting material is inserted into a bore of a cell housing and a force is applied from the interior of the tube outwardly against the wall of the tube so that the tube material is pressed against the cell housing and forms a connection therewith. The force may be applied by fluid pressure or, preferably, by drawing an appropriately shaped tool through the tube.

The resulting flow cell has a smooth inner surface with very good optical properties, so that light is guided through the cell substantially without loss. The flow cell can be manufactured with very long pathlengths (e.g. absorption path) without compromising light throughput. Furthermore, the invention ensures that the inner diameter of the tube of light guiding material has a uniform cross section along its length, thus contributing to improved optical properties. Also, the uniformity of the cross section ensures that the volume of the cell has a precisely determined value; this is advantageous, for example, for comparing measuring results obtained with different flow cells. Another advantage of the invention is that there is a very stable, form-fitting connection between the light guiding material and the cell housing. In that way changes of the flow cell geometry, for example due to expansion in connection with pressure variations, are avoided, thus leading to a substantial reduction of noise and wander effects in the detector.

According to an embodiment of the invention the tool which is drawn through the interior of the tube is heated, thus supporting the forming process. Alternatively or additionally, the tube material may also be heated.

In a preferred embodiment of the invention, an adapter is fixed to each of the two ends of the cell housing for closing the flow cell at the inlet and at the outlet. The adapters may comprise sample inlet and outlet channels, respectively, as well as pre-mounted optical fibers for introducing light into the flow cell and for conducting the light modified by the sample to a detection element.

The tube may be widened at the two end regions of the flow cell housing by a stamping tool such that it has the shape of a trumpet or funnel at these ends, and the adapter can then be used to jam the funnel-like parts between the cell housing and the adapters.

BRIEF DESCRIPTION OF THE DRAWINGS

In the following embodiments of the invention will be explained with reference to the drawings.

DETAILED DESCRIPTION

Figure 1:
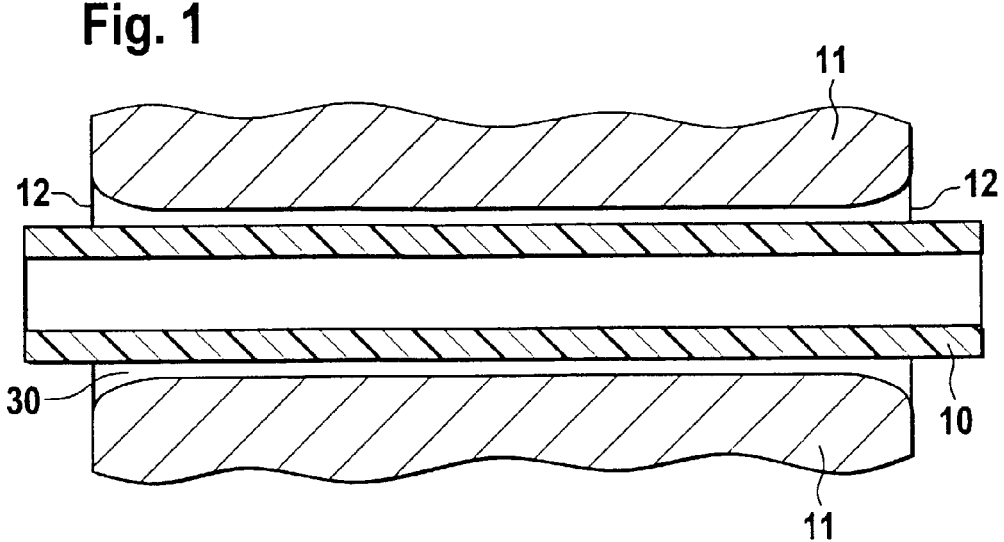
FIG. 1 illustrates a first method step for making a flow cell according to an embodiment of the invention.

As shown in FIG. 1, a tube 10 of Teflon AF is pushed into a cylindrical bore 30 of a cell housing 11. The housing 11 typically is a steel capillary and has machined end regions 12. The inner diameter of the housing, i. The diameter of the bore 30, is slightly larger than the outer diameter of the tube 10 such that it is just possible to insert the tube. Extruded Teflon AF tubes are available as semi-finished products from DuPont with an inner diameter of about 0.5 mm and an outer diameter of about 0.7 mm. The tube 10 projects from both ends of the housing 11 by about the same amount.

Figure 2:
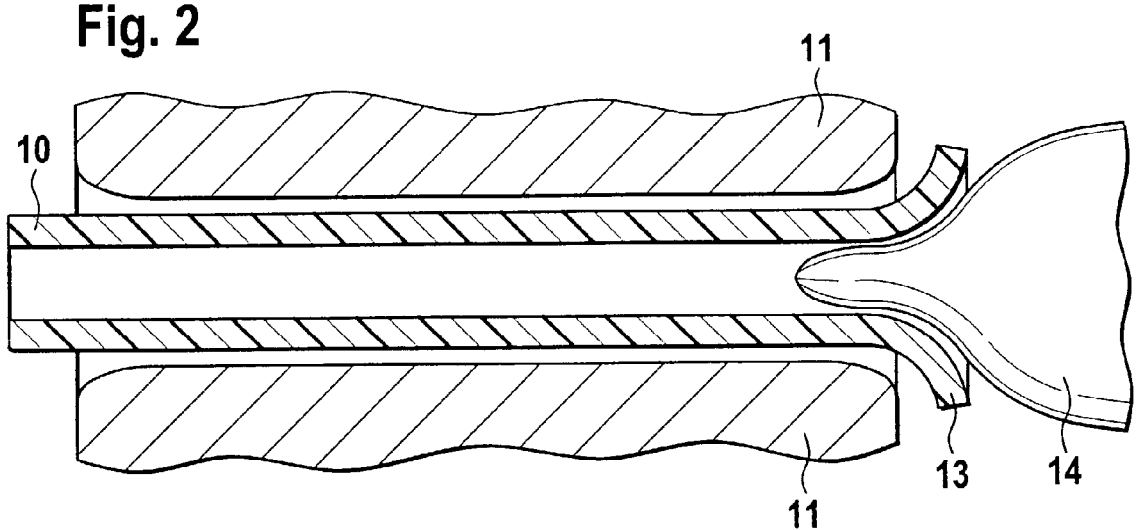
FIG. 2 illustrates a second step of the method of the invention, following the step shown in FIG. 1.

The housing 11 and one end of the projecting tube 10 are fixed with a special device (not shown). Then, as shown in FIG. 2, a heated stamping tool 14 is used to form the other end of the tube to a trumpet or funnel shape 13. During this forming step the housing 11 serves as support, wherein the end regions 12 of the housing have the desired trumpet shape.

Figure 3:
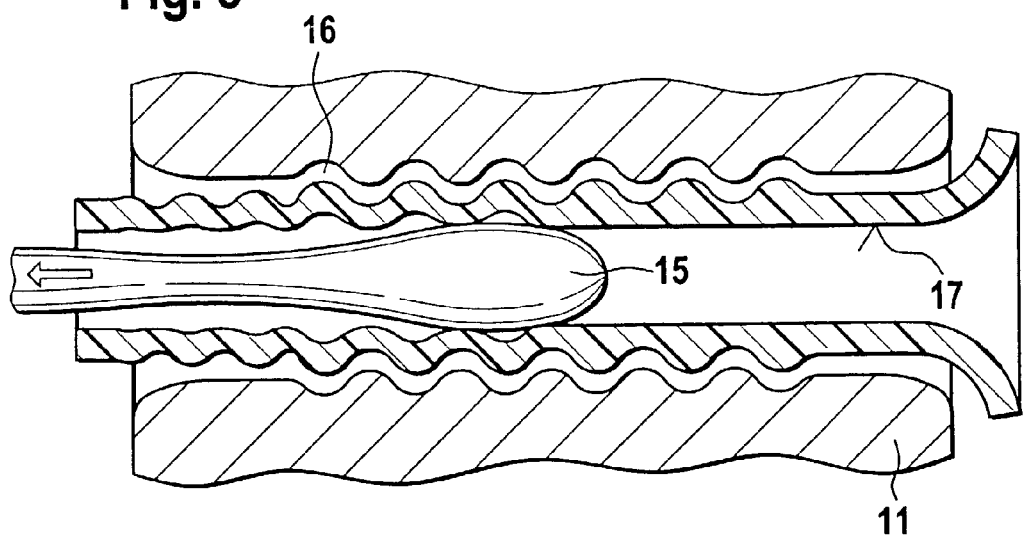
FIG. 3 illustrates a third step of the method of the invention, following the step shown in FIG. 2, wherein a mandrel is drawn through a Teflon AF tube.

In the next step, illustrated in FIG. 3, the mechanical fixing of the tube 10 within the housing 12 is performed. This is done by pressing the tube 10 from the interior against the inner wall of the housing 11. A heated mandrel 15 is drawn through the semi-finished tube 10 such that the tube is pressed against the housing 11. The mandrel 15 is a wire which has a drop shaped end region. The drawing of the heated mandrel through the tube causes a deformation of the tube so that it conforms to the interior wall of the housing 11. The Teflon AF material is forced into any chambers 16 in the surface of the housing 11, leading to a form-fitting connection between the tube 10 and the housing 11. The inner Teflon AF surface 17 is smooth and even, ensuring good optical performance, and the form-fitting connection between the Teflon AF material and the housing ensures mechanical stability of the sample cell so that pressure variations in the cell do not change the geometry of the cell which would lead to variations in the optical properties.

In the next step (not illustrated), the other end of the tube 10 (left side in FIG. 3) is also brought into the trumpet shape using the stamping tool 14.

Figure 4:
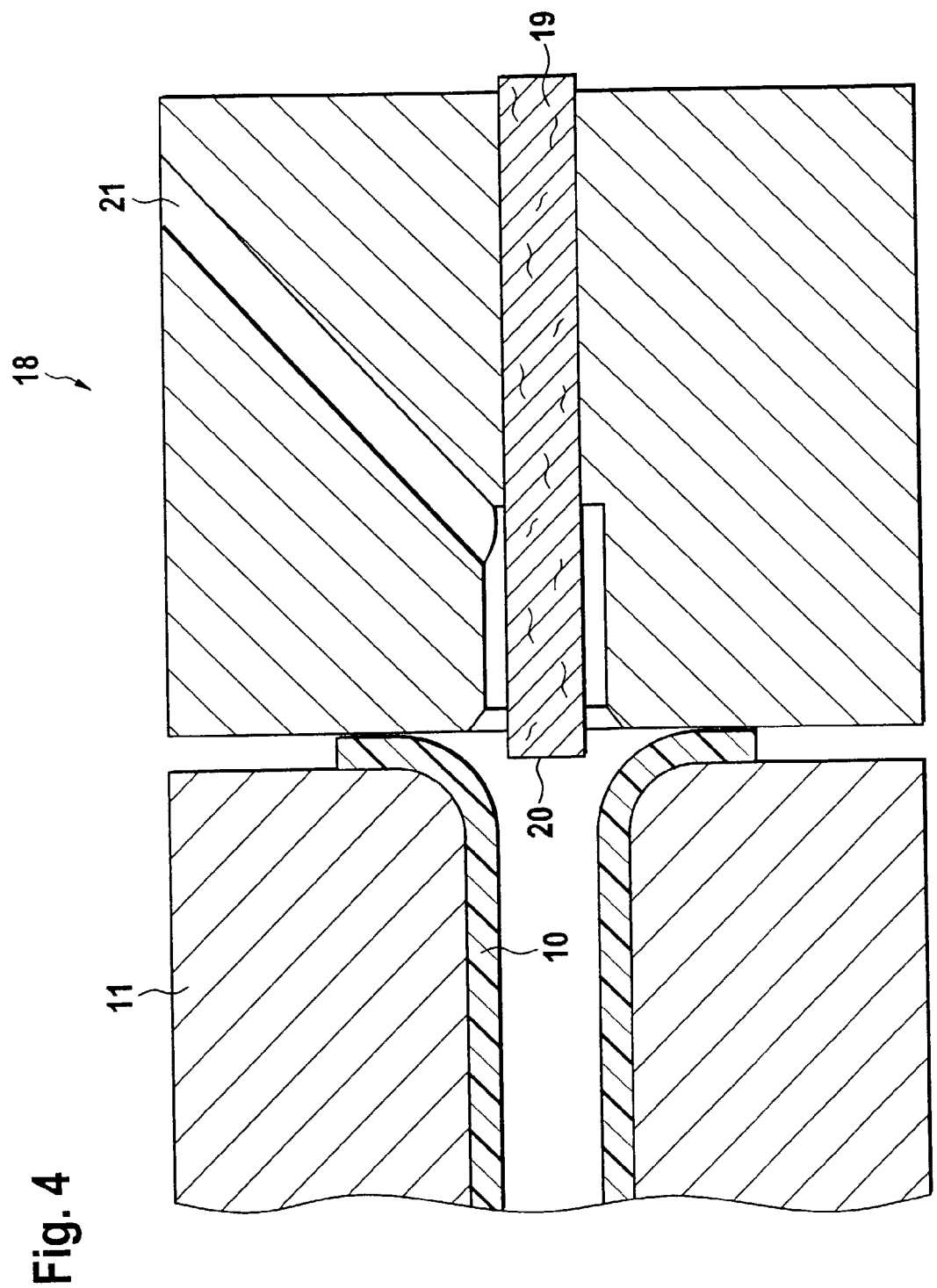
FIG. 4 illustrates a fourth step of the method of the invention, following the step shown in FIG. 3, wherein adapter pieces are fixed to the ends of the flow cell.

In the following manufacturing step, illustrated in FIG. 4, the thus processed cell piece is equipped with an adapter 18 on each side. The adapter 18 comprises an optical fiber 19 which has been fixed in a central bore of the adapter prior to mounting the adapter to the remaining cell piece. The optical fiber 19 is sealed against the adapter 18 so that liquid cannot escape between the fiber and the adapter. The end wall 20 of the optical fiber 19, as well as the end wall of the fiber on the other side, is polished. The fiber has an outer coating, except at the last few millimeters before the end face where the coating is removed.

Each of the two adapters 18 comprises a channel 21 through which the sample liquid to be detected enters or leaves the flow cell. These channels 21 are equipped with threads at their ends, respectively, so that standard fitting systems can be used for connecting liquid supply tubes.

The adapters are then mounted to each side of the cell piece, respectively, whereby the trumpet shaped Teflon AF parts 10 are jammed between the housing 11 and the adapter 18. In that way, a liquid tight seal is provided, with the outer surface of the trumpet sealing against the cell housing and the inner surface sealing against the adapter. An appropriate design of the cell housing and of the adapter ensures that the assembly of the parts can be performed without destroying them, see FIG. 4 and an alternative in FIG. 5. The position of the optical fiber 19 within the adapter 18 has been adjusted prior to mounting the adapter to the cell piece, thus determining the penetration depth into the Teflon AF tube or the distance from the tube. After the adapter has been fixed to the cell piece, for example by screws, the completed flow cell is ready for mounting to the measuring environment, for example to a spectrophotometer.

Figure 5:
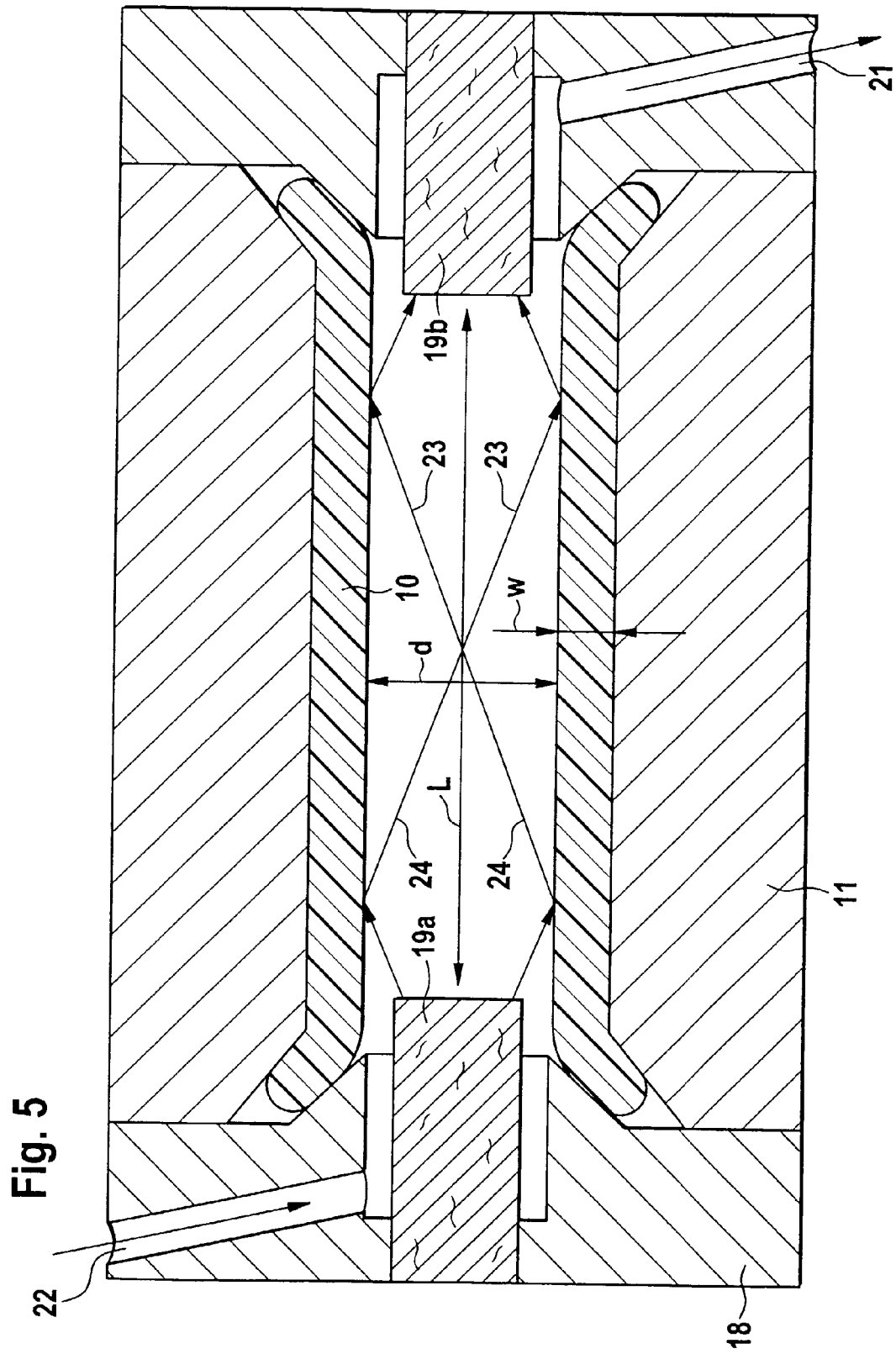
FIG. 5 is a cross sectional view of a flow cell manufactured according to an embodiment of the invention.

FIG. 5 shows a completed flow cell manufactured according to the invention with a housing 11, adapter 18, Teflon AF layer 10, optical fibers 19a and 19b, liquid inlet channel 22, and liquid outlet channel 21. The liquid flow through the cell is indicated by arrows 23. Some light rays exiting fiber 19a, being reflected at layer 10 and entering fiber 19b are designated with reference numeral 24. Compared to FIG. 4, FIG. 5 shows an alternative way of jamming the Teflon layer between housing 11 and adapter 18. Typical values of the inner diameter of the flow cell are ca. 100 to 800 micrometers and typical thicknesses for the Teflon AF layer are ca. 50 to 500 micrometers. The length of the flow cell may range from millimeters to meters.

In the following, some alternatives to the embodiment described above will be explained. Instead of using a mandrel for fixing the Teflon AF tube to the cell housing as shown in FIG. 3, it is also possible to use pressurized gas to press the Teflon layer against the cell housing. The pressurized gas, for example nitrogen, is introduced into the interior of the Teflon tube 10 so that the tube is "blown up" against the surrounding inner wall of the cell housing and leads to a form-fitting connection. The process can be improved by bringing the Teflon tube to an elevated temperature, either in a contactless manner or indirectly via the housing. As an alternative to using a gas for generating the increased pressure in the interior of the tube, a liquid could also be used.

It may be necessary to provide a structured inner surface of the housing so that the surplus material of the Teflon AF tube can escape to the outside during the forming process so that the material is not drawn all along through the cell. For this purpose, it is advantageous to build the cell housing from two or more separate parts which comprise chambers or recesses on one or more parts for receiving Teflon material. By using, for example, a plurality of disks or rings which are linked together, a very high aspect ratio (i.e. ratio of length to diameter) can be achieved.

The mandrel used in the forming process in the interior of the Teflon tube can be made of any suitable material. For example, a glass rod could also be used. Not only the mandrel may be held at an elevated temperature during the forming process, but also the Teflon tube, e.g. with an infrared radiation source.

As a further alternative, the inner bore of the Teflon AF tube could have an oval or rectangular cross section. Also, it is not necessary that the tube is widened (e.g. like a trumpet) at the end regions of the cell; the end regions may have, like the rest of the tube, an essentially cylindrical shape.

As an additional alternative, instead of using optical fibers for conducting light to or from the cell bore, optical windows could also be used as part of the adapter pieces. Especially with this alternative the tube widening (e.g. trumpet-shaped) may not be necessary.

What is claimed is:

1. A method of manufacturing a flow cell that includes a cell housing with a bore for the passage of a sample and an inner layer of a polymer material for guiding radiation through said bore for analysis of the sample, the method comprising:

provinding a tube having said inner layer of said polymer material in said bore of said cell housing; and applying a force on said inner layer of said tube from the interior of said tube for pressing walls of said tube against said cell housing, thereby providing an inner surface for providing total reflection and thus guiding radiation through said bore.

2. The method as in claim 1, wherein the application of force is performed by drawing a mandrel through the interior of said tube.

3. The method as in claim 2, wherein said mandrel is drop shaped.

4. The method as in claim 1, wherein the application of force is performed by providing increased pressure in the interior of said tube.

5. The method as in claim 1, wherein said tube is widened at the first and/or second end regions of said cell housing.

6. The method as in claim 2, wherein said mandrel is at an elevated temperature.

7. The method as in claim 1, wherein said tube is at an elevated temperature.

8. The method as in claim 1, wherein said cell housing comprises a first and second end region disposed at opposite ends of said cell housing and further comprising an adapter affixed to each of said first and second end regions.

9. The method as in claim 5, wherein the widened end of said tube is disposed between said cell housing and an adapter.

10. The method as in claim 9, wherein said adapter comprises a flow channel serving as a sample inlet or outlet.

11. The method as in claim 8, wherein an optical fiber is arranged in said adapter prior to affixing said adapter to said cell housing.

12. The method as in claim 8, wherein an optical window for conducting radiation to or from said cell bore is arranged in said adapter.

13. The method as in claim 1, wherein said cell housing comprises a plurality of parts, wherein at least one of said plurality of parts comprises a chamber for receiving polymer material, and wherein each said chamber forms at least a portion of said bore.

14. The method as in claim 13, wherein said polymer material is an amorphous fluoropolymer.

* * * * *